United States Patent [19]
Sullivan et al.

[11] Patent Number: 5,723,305
[45] Date of Patent: Mar. 3, 1998

[54] MARKER FOR MALE INFERTILITY AND/OR FERTILITY

[76] Inventors: Robert Sullivan, 3261 Chemin St-Louis, Ste-Foy, Québec, Canada, G1V 1S1; Franck Boué, 15 avenue Raspail, 94250 Gentilly, France

[21] Appl. No.: 634,340

[22] Filed: Apr. 18, 1996

[51] Int. Cl.⁶ .............................. G01N 33/53; C07K 16/28
[52] U.S. Cl. .......................... 435/7.21; 435/7.9; 435/806; 435/810; 435/975; 436/906; 530/388.2; 530/388.85; 530/389.1; 530/391.3
[58] Field of Search ...................... 435/7.1, 7.2, 7.21, 435/7.7, 7.9, 40.51, 806, 975, 810; 530/387.1, 391.3, 388.2, 388.85, 389.1; 436/906

[56] References Cited

PUBLICATIONS

Sullivan et al. (1995) Colloque INSERM, vol. 236 (0): 416–417.

Bérubé B. et al., 1994, *Bio Reprod.*, 51:1255–1263.

Boué F. et al., 1994, *Biol. Reprod.*, 51:577–587.

Liu D.Y. et al., 1992, *Fertil. Steril.*, 58:465–483.

*Primary Examiner*—Christina Y. Chan
*Assistant Examiner*—Emma Cech
*Attorney, Agent, or Firm*—Swabey Ogilvy Renault

[57] ABSTRACT

The present invention relates to a method for the diagnosis of male infertility which comprises the steps of a) determining the amount of P34H in a sperm sample; and b) comparing the determined amount of step (a) with a fertile control sample. The present invention also relates to a kit for the diagnosis of male infertility which comprises an anti-P34H antibody enzyme-labeled, an enzyme substrate and a fertile control sample.

2 Claims, 4 Drawing Sheets

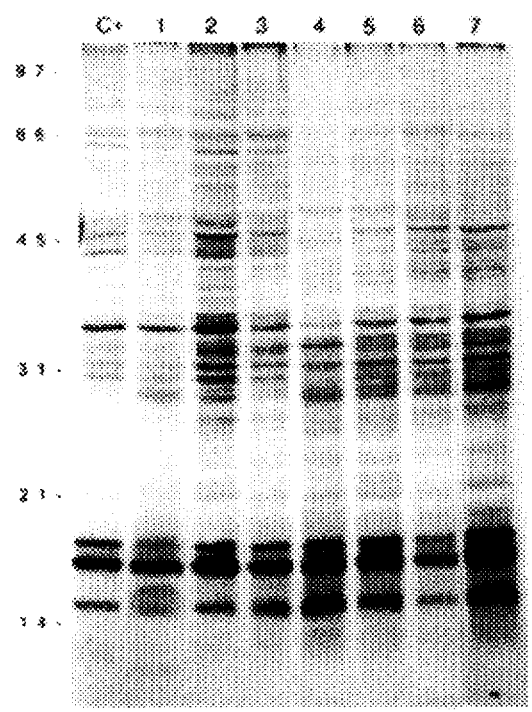
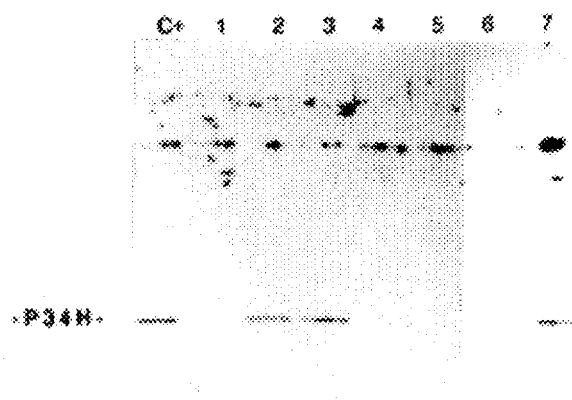
FIG. 1A
FIG. 1B

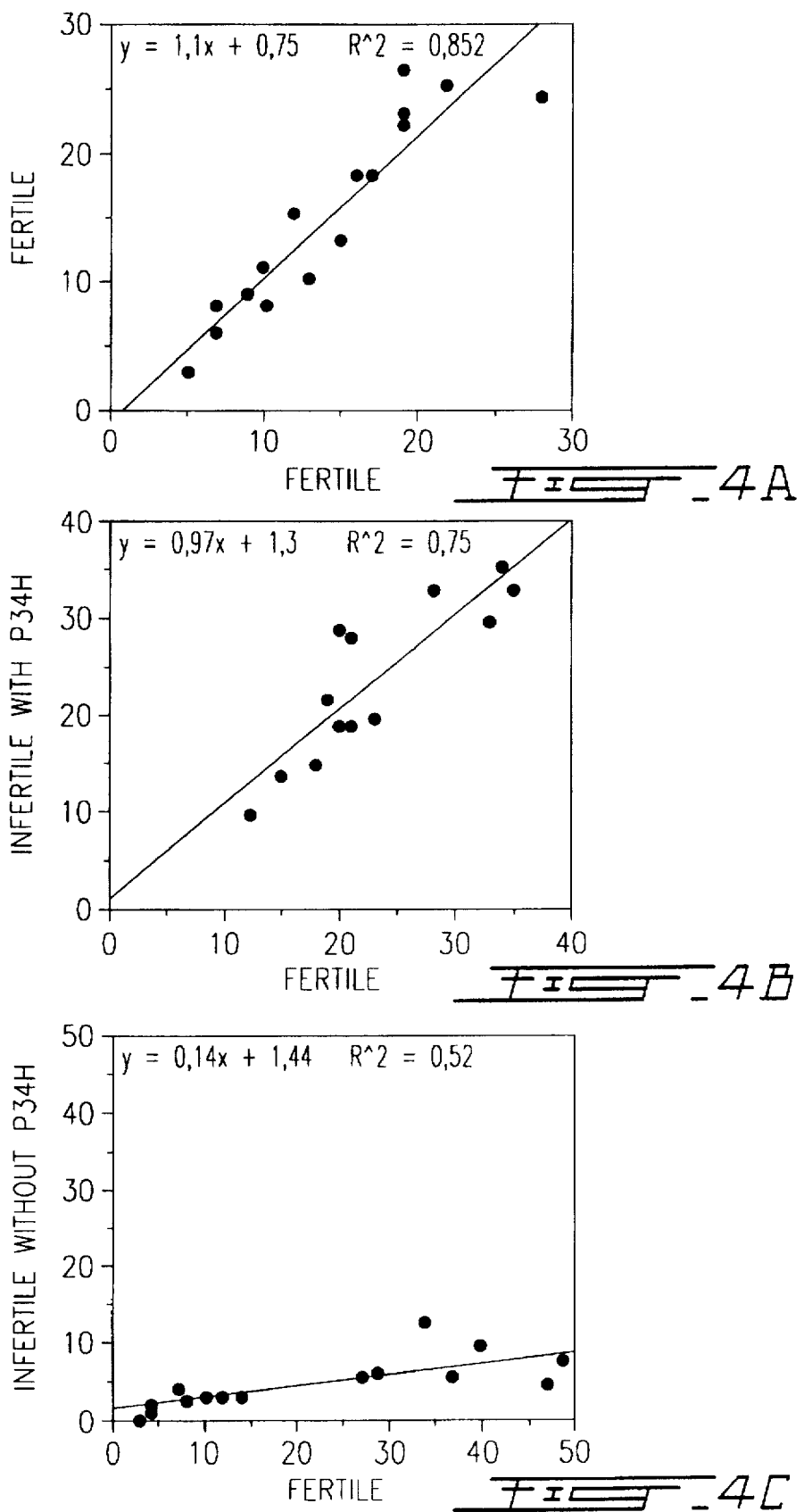

MARKER FOR MALE INFERTILITY AND/OR FERTILITY

BACKGROUND OF THE INVENTION (a) Field of the Invention

The invention relates to a marker for male infertility and/or fertility and to a method for the diagnosis of male infertility.

(b) Description of Prior Art

Infertility occurs in approximately 8% of North American couples. In 50% of these cases, male factors contribute to this pathological situation. Standard semen analysis including sperm concentration, motility, and morphology are widely used as principal indicators of male fertility. However, these parameters fail to explain all cases of male infertility and do not provide a precise prognostic value of human fertility in vivo or in vitro. Due to the fact that standard semen parameters often provide a poor prognostic value, many other laboratory tests have been developed in order to evaluate the fertilizing ability of human spermatozoa. These include the determination of sperm membrane integrity by hypoosmotic swelling test, nuclear maturity, acrosomal status, motility assessment by video-imaging as well as the ability of sperm to interact with the oocyte. This sperm function has been evaluated by the zona-free hamster test and by the ability of human spermatozoa to bind to homologous zonae pellucida. Therapeutic in vitro fertilization represents a direct evaluation of the fertilizing ability of semen. The prognostic value of the various andrology tests can thus be determined by correlating their conclusions with in vitro fertilization results. The relationship between the different tests and fertilization rates in vitro have shown a very high correlation with the ability of sperm to bind to the zona pellucida, whereas normal morphological sperm and linearity of motility correlated with a lower significance. Other sperm parameters have been shown to be of no prognostic value (Liu D. Y. et al., 1992, *Fertil. Steril.*, 58:465-483). While morphology and linearity are sperm parameters that could easily be assessed, the sperm-zona pellucida binding assay is difficult to perform mainly due to the limited availability of human zonae pellucidae and the technical difficulties associated with a large inter-assay variability.

The binding of sperm to the zona pellucida is an absolute prerequisite for fertilization in man as well as in other mammalian species and appears to be species-specific. The failure of sperm-zona pellucida binding may be associated with certain cases of male infertility. Therefore, laboratory tests that evaluate the ability of sperm to undergo successfully this step in gamete interaction could have clinical usefulness in the diagnosis of male infertility.

Using different animal models, it has been shown that during epididymal transit the male gamete acquires its fertilizing ability. During this maturational process, sperm surface proteins are added or modified and these modifications are involved in the acquisition of the ability to the spermatozoa to bind to the zona pellucida.

A 34kDa human epididymal sperm protein (P34H) was previously described and it was proposed to be involved in the interaction of human spermatozoa and the homologous zona pellucida (Boué F. et al., 1994, *Biol. Reprod.*, 51:577-587). P34H appears on the acrosomal cap of the spermatozoa within the caput epididymis. Furthermore, a polyclonal antibody against P34H interferes with the ability of spermatozoa to bind the human zona pellucida, without affecting motility, the acrosome reaction and the fusion with the plasma membrane of the oocyte. Thus, P34H appears to be involved in one of the absolute prerequisites of fertilization, i.e. sperm-zona pellucida binding.

It would be highly desirable to be provided with a marker for male infertility and/or fertility.

It would be highly desirable to be provided with a method for the diagnosis of male infertility.

SUMMARY OF THE INVENTION

One aim of the present invention is to provide a marker for male infertility and/or fertility.

Another aim of the present invention is to provide for a method for the diagnosis of male infertility.

In accordance with the present invention there is provided a method for the diagnosis of male infertility which comprises the steps of:

a) determining the amount of P34H in a sperm sample; and b) comparing the determined amount of step a) with a fertile control sample.

The amount of P34H in step a) may be determined using an antibody raised against P34H.

In accordance with the present invention there is provided a kit for the diagnosis of male infertility which comprises:

a) an anti-P34H antibody enzyme-labeled;

b) an enzyme substrate; and c) a fertile control sample.

A calibration curve for the amount of P34H may be obtained using the fertile control sample of component (c) above

BRIEF DESCRIPTION OF THE DRAWINGS

FIGS. 1A and 1B illustrate silver stained (FIG. 1A) and corresponding immunoblots (FIG. 1B) probed with anti-P34H antiserum of SDS-PAGE of proteins extracted from $5.10^6$ human spermatozoa from fertile men (C+) and infertile men (1-7);

FIGS. 4A-4C are Western blot analyses of the number of spermatozoa from control fertile donor (X axis) or from different men (Y axis) bound per human zona pellucida.

DETAILED DESCRIPTION OF THE INVENTION

Figure 2:
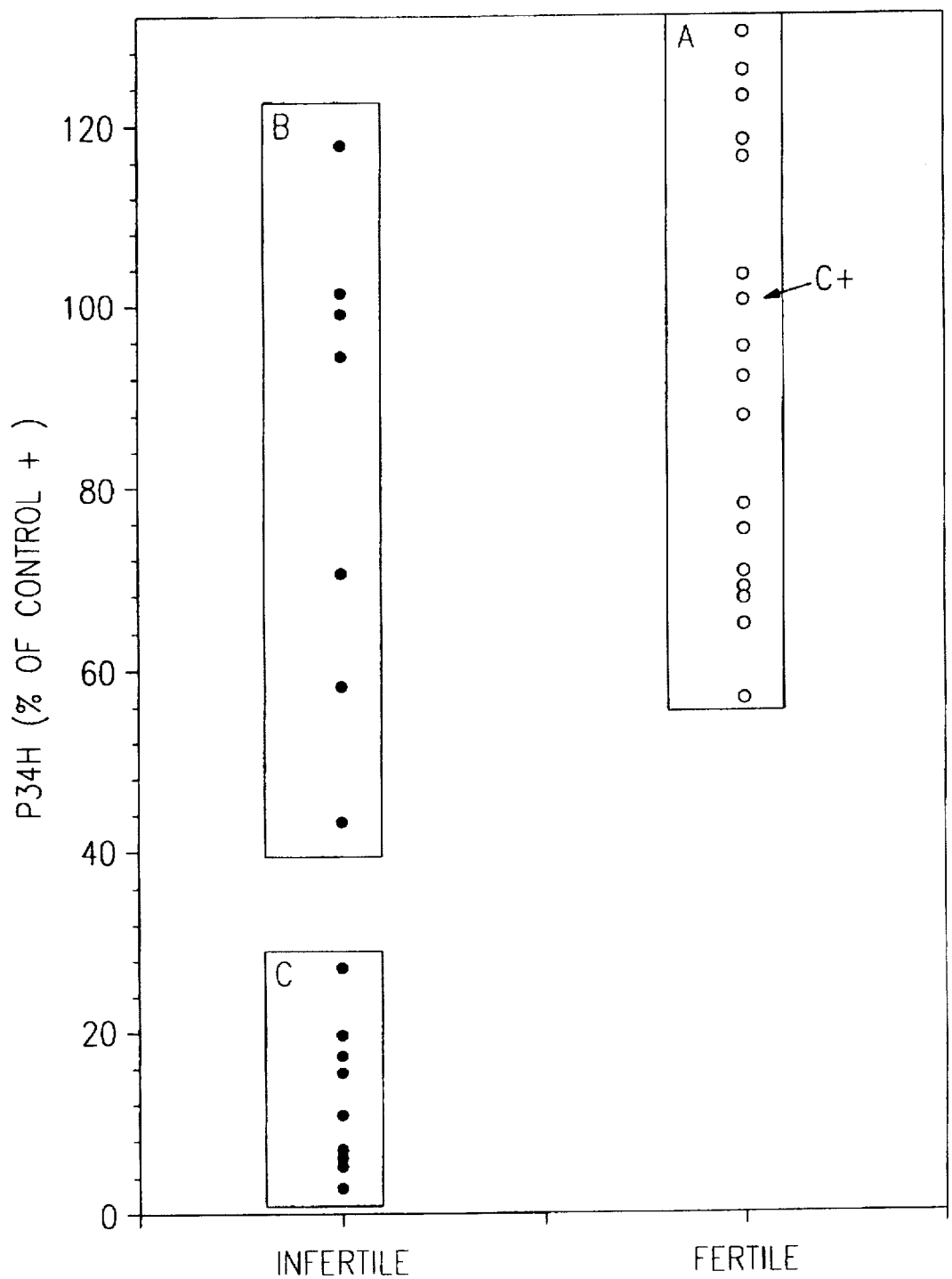
FIG. 2 is an analysis of amounts of P34H as determined by densitometric scan of immunoblots of proteins extracted from $5.10^6$ spermatozoa from fertile (○) and infertile (●) men.

The interaction of spermatozoa with the zona pellucida is a critical step of fertilization. Specific sperm surface proteins involved in this process could be added or modified during epididymal transit. A 34 kDa human epididymal sperm protein (P34H) was proposed to be involved in sperm-zona pellucida interaction. In this study, Western blot analyses were performed to determine the level of P34H protein present on the spermatozoa of 16 men with idiopathic infertility. These levels were compared with the amount found in men of proven fertility. In addition, a sperm-zona pellucida binding assay was performed with spermatozoa from fertile and infertile men. Individual men have similar P34H levels on their spermatozoa obtained from different semen samples. However, the amount of P34 varied from one man to another. Compared to a population of fertile men, 9/16 infertile men had a P34H level of less than 30% of the normal value, while the remaining 7 males were in the normal range. Sperm from infertile subjects with a normal P34H determination bound to the zonae pellucidae as efficiently as fertile controls. However, spermatozoa from subjects with a low amount P34H exhibited a dramatic diminution in their ability to interact with zonae pellucidae. The results show that the quantity of the epididymal protein, P34H, varied from one male to another and that low levels of this epididymal sperm protein are associated with certain cases of idiopathic infertility.

Spermatozoa Collection Procedure

Sixteen couples presenting with primary infertility were included in this study. Infertility was defined by a period of at least 30 months of unprotected sexual intercourse. In all cases, infertility was classified as idiopathic based on a full infertility work-up. In women, clinical investigation included: negative hysterosalpingography and laparoscopy, normal ovulation as evaluated by basal body temperature, plasma hormone concentrations, normal endometrial biopsy and post-coital test. The men had produced at least three normal spermiograms as defined by the WHO criteria and were free from anti-sperm antibodies as determined by a negative immunobead test. These healthy men were between 23 and 39 years of age, a group comparable to the group of fertile volunteers used in this study. The latter had fathered a child less than 3 years prior to this study and had shown normal spermogram values in accordance with WHO standards. Between two and seven days of sexual abstinence was required before semen was collected by masturbation. After a liquefaction period of 30–60 min. at room temperature, the usual spermogram values were determined before processing the semen samples. No correlation could be established between these values and the levels of P34H as determined in a constant number of spermatozoa from each sample. Spermatozoa were washed three times by centrifugation (800 g) in D-PBS (Dulbecco-phosphate buffered saline: Gibco) and resuspended in SDS-PAGE sample buffer (50 mM Tris-HCl buffer, pH 6.8, 2% sodium dodecyl sulfate and 5% b-mercaptoethanol at a final concentration of $5.10^5$ spermatozoa/μl. These samples were heat denatured at 95° C. for three min., centrifuged at 14 000 g and supernatants were kept at −20° C. until used.

To compare spermatozoa with different buoyant densities, aliquots of semen samples were loaded onto a discontinuous Percoll™ gradient. This gradient was composed of two layers of Percoll™ (90% and 45%) prepared in D-PBS. After centrifugation at 1 300 g, spermatozoa were collected at the 45–90% Percoll interface and in the pellet below the 90% Percoll layer. Spermatozoa were washed in D-PBS and were resuspended in sample buffer at the final concentration of $5.10^5$ spermatozoa/μl and processed as described above.

Western Blot Analysis

Proteins from $5.10^6$ spermatozoa from each semen sample were submitted to electrophoresis in presence of sodium dodecyl sulfate on a 12% acrylamide gel. The gels were stained with silver nitrate or electro-transferred to nitrocellulose membranes. These Western blots were saturated for two hours in PBS containing 10% defatted milk and 2% normal goat serum followed by an overnight incubation with the anti-P34H antiserum diluted 1:1000 in PBS supplemented with 1% goat serum. Three volumes of anti-P34H poly-clonal antiserum was first adsorbed overnight on one volume of powder of human keratin. After three washes with 0.1% (V/V) Tween™ 20 in PBS, nitrocellulose membranes were incubated for 1 hour with a peroxidase-conjugated anti-rabbit IgG (1/3000 in PBS) and washed three times with PBS-Tween™. Immune complexes were detected with a BioMax™ film (Kodak) following incubation with a chemiluminescent substrate of peroxidase (ECL Kit; Amersham, Buckinghamshire, UK) according to the supplier's instructions.

Quantification of P34H

In order to quantitate the P34H level, three independent Western blots of each sperm sample were scanned using an LKB UltroScan XL™ Laser Densitometer. The surface under the curve corresponding to the amount of P34H in each sample of $5.10^6$ spermatozoa was determined and expressed as a percentage of an internal positive control. The latter consisted of a sperm sample from a healthy donor in which the level of P34H was defined as 100%. In each Western blot, a sperm sample from this donor was processed in parallel in order to serve as an internal standard.

Human Sperm-Zona Pellucida Binding

Human sperm-zona pellucida binding assays were performed with spermatozoa labeled with two different fluorochromes. In this study, human oocytes obtained in the context of therapeutic in vitro fertilization and that had remained unfertilized after 48–60 h post insemination were stored in liquid nitrogen. Immediately prior to use, oocytes were washed by transfer into five successive baths of D-PBS containing 0.5% BSA (bovine serum albumin, fraction V) followed by a final wash in B2 medium (Bio Merieux, Marcy-L'Étoile, France). Semen samples were submitted to a discontinuous Percoll gradient as described above. Motile spermatozoa, recovered in the pellet under the 90% Percoll layer, were capacitated in B2 medium at 37° C. in 5% $CO_2$ for 3 hours. Spermatozoa prepared from semen of different men were labeled with one of the two fluorochromes FITC (fluorescein) or TRITC (tetramethylrhodamine isothiocyanate). Spermatozoa from a fertile donor that were used as a control were labeled with the other fluorochrome. After labeling, spermatozoa were washed and resuspended in B2 medium at a final concentration of $2.10^5$ motile spermatozoa/ml. Equal volumes of FITC and TRITC labeled spermatozoa were mixed and incubated at 37° C. in 5% $CO_2$ with human zonae pellucidae. Two hours later, the zonae pellucidae were extensively washed by successive pipetting and individually observed under an epifluorescence microscope at the appropriate wavelength corresponding to FITC and TRITC in order to determine the number of spermatozoa from each category that bound to the zona pellucida.

Statistical Analysis

The distribution-free test U of Mann and Whitney was performed to evaluate the difference in the level of P34H between the two populations of infertile and fertile men. Human sperm-zona pellucida binding assays were studied by linear regression analysis, and compared to the theoretical line by the Student "t" test.

Results

Silver stained electrophoretic patterns of sperm proteins from different semen samples are illustrated in FIG. 1A.

Molecular weight standards ($10^3$ kDa) are indicated on the left. Minor differences in the protein patterns were observed from one sample to the other while the overall protein solubilized under reducing conditions were consistent in all samples. Although the patterns of proteins were similar, the corresponding Western blots probed with the anti-P34H revealed dramatic differences in the amount of this particular sperm antigen (FIG. 1B). Western blotting was necessary to detect these differences due to the fact that P34H, which is a very minor sperm protein, cannot be detected in the stained electrophoretic protein patterns, in spite of the use of the highly sensitive silver staining procedure (FIG. 1A).

Western blots probed with anti-P34H antiserum exhibited a single band at 34 kDa corresponding to P34H. Whereas the electrophoretic mobility of P34H was similar from one sample to the other, the intensity of this band was highly variable (FIG. 2). The results are expressed as a percentage of an internal positive control (C+=100%). Group A and Group B were similar, whereas, Group C was significantly different from group A (p<0.001). Western blotting was performed on a constant number of spermatozoa obtained from 16 subjects presenting with idiopathic infertility as well as from 17 fertile donars. When quantified by densitometric scanning, the levels of P34H in fertile donors varied between 57% and 129% in comparison to the internal positive control ($C^+$) representing 100%. On the other hand, the levels of P34H in those samples obtained from infertile patients were between 3% and 117%. Two populations of infertile patients were therefore defined according to the amount of P34H detected. Those with a P34H value lower than 30% were significantly different from the control fertile group with a P<0.001. Idiopathic infertile men with higher values of P34H were comparable to the fertile group. Thus, 9 out of 16 infertile men with normal spermogram values were characterized by values of P34H that were significantly lower than the fertile group.

Figures 3A, 3B:
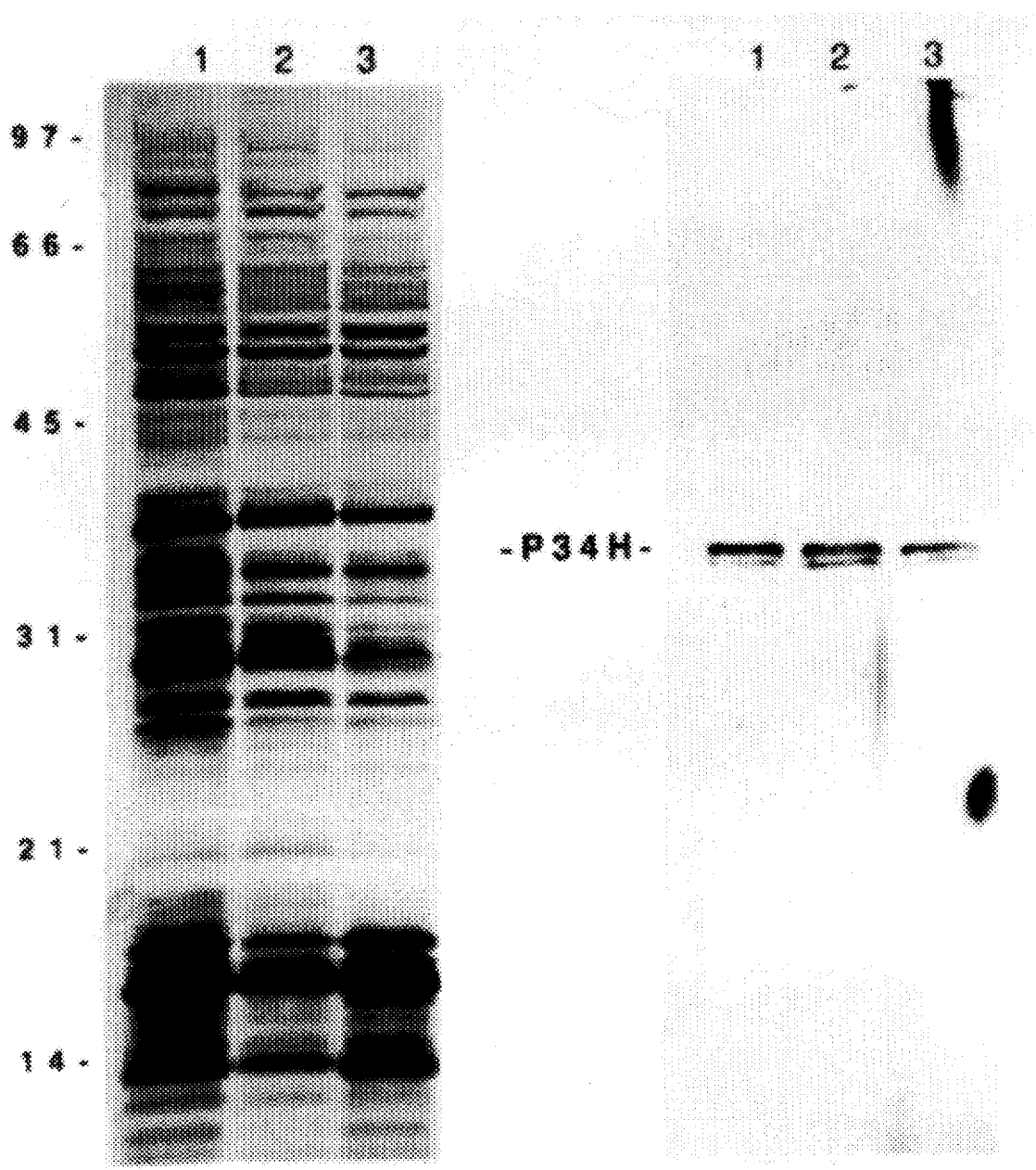
FIGS. 3A-3B illustrate silver stained (FIG. 3A) and corresponding immunoblots (FIG. 3B) probed with anti-P34H antiserum of SDS-PAGE of proteins extracted from $5.10^6$ human spermatozoa from fertile men before (1) or after a discontinuous Percoll centrifugation (2,3)

In order to ascertain whether variations in the P34H levels could be associated with certain cases of infertility rather than with an intersample variability, we have determined this parameter on a constant number of sperm from more than one semen sample collected from different men. This data demonstrated that the expression of P34H was constant from one semen sample to the other in any one individual (Table 1). This was true for fertile men as well as for infertile men that expressed or did not express P34H on their spermatozoa. Even though the case history of PGO and JLA were similar, the amount of P34H that characterized these two infertile men was quite different. Spermatozoa from semen samples separated by Percoll gradient centrifugation also exhibited comparable P34H values even though they were characterized by different buoyant densities (FIG. 3).

TABLE 1

P34H determination in different semen samples from fertile and infertile men

| | Semen sample | P34H (% of control +) | Mean |
|---|---|---|---|
| Fertile | | | |
| #1 | 2 | 125% | 108% |
| | | 91% | |
| #2 | 2 | 100% | 107.5% |
| | | 115% | |
| Infertile | | | |
| PGO | 2 | 92% | 102.5% |
| | | 113% | |
| JLA | 2 | 8% | 9% |
| | | 10% | |

In order to correlate the presence of P34H with fertilizing ability, we have performed in vitro zona pellucida binding assays using spermatozoa with various levels of P34H. Each zona pellucida was inseminated with sperm from a fertile donor along with the same number of sperm from a second fertile donor (FIG. 4A), as well as with sperm obtained from infertile men with a normal level of P34H (FIG. 4B) or infertile men with low levels of P34H (FIG. 4C). The Y axis corresponds to fertile (A), infertile men with (B) or without (C) P34H. Each value corresponds to one zona pellucida. The regression line corresponding to each panel is illustrated. The number of sperm from each experimental group (Y axis in FIG. 4) was compared with the internal fertile control (X axis in FIG. 4). Simple regression analysis of each experiment indicated that the evaluation of the sperm binding ability by the double staining technique used was consistent from one zona pellucida to another with a significance of p<0.002 (Table 2).

TABLE 2

Statistical analysis of *zona pellucida* binding ability of spermatozoa from fertile and infertile men

| | Linear regression equation | r.squared | simple regression probability | linear regression vs. theoretical line significant difference |
|---|---|---|---|---|
| theoretical (median) | Y = 1X | 1 | | |
| Fertile/Fertile | Y = 1.1X − 0.75 | 0.85 | P < 0.001 | NS |
| Fertile/infertile with P34H | Y = 0.97X + 1.3 | 0.75 | P < 0.001 | NS |
| Fertile/infertile without P34H | Y = 0.14X + 1.44 | 0.52 | P < 0.002 | P < 0.001 |

This allowed the comparison of the regression line calculated from each experiment with a theoretical line where all zonae pellucidae would be on the median e.g. an ideal situation where each spermatozoon on the Y axis shows the same binding ability as those from a positive fertile control on the X axis. In this situation, only the comparison of the sperm binding ability between fertile positives and infertile subjects without P34H (FIG. 4C) showed a highly significant difference at $P<0.001$. Thus, spermatozoa with normal levels of P34H had the same ability to bind to zonae pellucidae regardless of the fertility status of the donor. Compared to healthy donors, spermatozoa obtained from males without P34H showed a highly significant decrease in their ability to bind to the zona pellucida with a $P<0.001$ (Table 2).

Discussion

During the past 15 years the increasing investigation of the causes of infertility has shown that male reproductive dysfunctions are primary factors in up to 40% of those couples consulting for infertility. Standard semen analysis including sperm concentration, motility and morphology have provided relevant clinical information mainly in those extreme cases of male infertility such as azoospermia, severe oligo-astheno-spermia and total terato or necrospermia. However, in the majority of cases, the usual spermiogram parameters have low prognostic values for the in vivo and in vitro fertilizing capacity of spermatozoa. In vitro fertilization is useful to evaluate sperm function but cannot be used for diagnostic purposes. Many new functional tests have thus been developed and used to evaluate the fertilizing capacity of human sperm. Although some of these are recommended by the WHO, they provide limited information with regard to fertilization and are of questionable prognostic value. It would appear that those experimental procedures that evaluate the ability of spermatozoa to bind to homologous zona pellucida have a high correlation with fertilization potential (Liu D. Y. et al., 1992, Fertil. Steril., 58:465-483).

The binding of spermatozoa to the homologous zona pellucida involves a receptor on the male gamete with a high affinity for its ligand. In the hamster, we have previously identified a sperm protein, P26h, that meets many criteria that are essential in order to be considered as a zona pellucida receptor (Bérubé B. et al., 1994, Bio. Reprod., 51:1255-1263). Using antibodies raised against P26h we have recently identified a human sperm protein, P34H, that shows antigenic and functional homologies with the hamster P26h (Boué F. et al., 1994, Biol. Reprod., 51:577-587). We have thus proposed that P34H is involved in the processes mediating sperm-zona pellucida interaction in humans.

P34H is localized on the surface covering the acrosomal cap of ejaculated human spermatozoa (Boué F. et al., 1994, Biol. Reprod., 51:577-587); a localization that is in agreement with the proposed function. In fact, it is via this subcellular region that the male gamete interacts with the zona pellucida. The amount of P34H found on a constant number of spermatozoa was highly variable from one individual to the other (FIGS. 1 and 2). Interestingly, the protein is present on spermatozoa of all these fertile men that were investigated while lower amounts of this sperm antigen were encountered only in normospermic infertile men (FIG. 2). This observation is in agreement with the proposed function of P34H and the fact that the sperm zona binding ability is of high prognostic value for male fertility (Liu D. Y. et al., 1992, Fertil. Steril., 58:465-483). This is directly demonstrated by the fact that spermatozoa from fertile as well as from infertile men with normal P34H values are able to bind to homologous zona pellucida whereas spermatozoa from infertile men with low levels of P34H are unable to interact with the egg's extracellular coat (FIG. 4 and Table 2). Considering that the presence of sufficient amounts of P34H can be correlated with human sperm ability to bind to the zona pellucida, this sperm antigen could thus be considered as a biochemical marker of male fertility. In this regard, it is important to note that the variability of P34H is due to an inter-individual variability and that this parameter is consistent from one semen sample to the other from the same individual (Table 1). The variation of P34H on spermatozoa of different buoyant densities could not explain the important variation of P34H level found in our group of infertile men (FIG. 3). Two populations of idiopathic infertile men can be defined on the basis of P34H levels. Over 50% (9/16 in this study) of men presenting with idiopathic infertility are characterized by low levels of P34H (group C in FIG. 2) and spermatozoa from the latter group are unable to bind to zona pellucida (FIG. 4C and Table 2). It is obvious that infertility is a multifactorial disease and the absence of one sperm antigen cannot account for all of those cases of unexplained male infertility. Nevertheless, a high proportion of these men from infertile couples investigated in this study show an abnormally low level of P34H.

P34H is a biochemical marker that could be readily used for the diagnosis of male infertility. In these cases, infertility is associated with the inability of the spermatozoa to interact efficiently with the zona pellucida. The rather high occurrence of this defect in our normospermic infertile man population suggests that dysfunction may be a common cause of infertility. In vitro fertilization is presently applied to overcome certain cases of male infertility. Compared to the results obtained when these technologies are applied to overcome tubal diseases, the chances of successful in vitro fertilization applied to male infertility is much lower. Thus, the determination of P34H levels could be relevant by avoiding clinical procedures that cannot overcome the inability of the spermatozoa to penetrate the egg investments in vivo as well as in vitro.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method for the diagnosis of male infertility which comprises the steps of:
   a) determining the amount of P34H, a 34 kDa human epididymal sperm protein, in a sperm sample using an antibody specific to P34H; and
   b) comparing the determined amount of step a) with a fertile control sample, wherein a P34H value lower than 30% of the fertile control sample is indicative of infertility.

2. A kit for the diagnosis of male infertility which comprises:
   a) an anti-P34H antibody enzyme-labeled;
   b) an enzyme substrate; and
   c) a fertile control sample.

* * * * *